United States Patent [19]

Wei et al.

[11] 4,293,696

[45] Oct. 6, 1981

[54] 3-SUBSTITUTED PHENYLTHIAZOLO[3'2':1,2]IMIDAZO[4,5-B]PYRIDINE-2-ALKANOIC ACIDS

[75] Inventors: Peter H. L. Wei, Springfield; Stanley C. Bell, Penn Valley, both of Pa.

[73] Assignee: American Home Products Corporation, New York, N.Y.

[21] Appl. No.: 218,903

[22] Filed: Dec. 22, 1980

[51] Int. Cl.³ .................................................. C07D 513/14
[52] U.S. Cl. ........................................ 546/83; 424/256
[58] Field of Search ............................................ 546/83

[56] References Cited

U.S. PATENT DOCUMENTS 3,932,395  1/1976  Hideg et al. ................... 546/83 X

OTHER PUBLICATIONS

Bell et al., Journal of Medicinal Chemistry, vol. 19, No. 4, (1976), pp. 524-530.

Primary Examiner—Richard Raymond
Attorney, Agent, or Firm—George Tarnowski

[57] ABSTRACT

3-Substituted phenythiazolo[3'2':1,2]imidazo[4,5-b]pyridine-2-alkanoic acids and their use as immunomodulating agents are disclosed.

2 Claims, No Drawings

3-SUBSTITUTED PHENYLTHIAZOLO[3'2':1,2]IMIDAZO[4,5-B]PYRIDINE-2-ALKANOIC ACIDS

BRIEF DESCRIPTION OF THE INVENTION

The invention relates to 3-substituted phenylthiazolo[3'2':1,2]imidazo[4,5-b]pyridine-2-alkanoic acids and their use as immunomodulating agents.

Immunodeficiency has been considered as an important factor in oncogenesis, autoimmune disease, and genetic disposition to infections, and so forth. Chemical agents capable of stimulating the cellular and/or humoral responses have been employed in the therapeutical treatment of such disorders. Immunomodulators which exert an immunostimulatory effect on the immune response can assist in the therapeutic stimulation of cellular immunity, and so are useful in the treatment of diseases involving chronic infection in vivo, such as fungal or mycoplasma infections, tuberculosis, leprosy, acute and chronic viral infections and the like. By stimulating T cell production, such compounds can be used to overcome T cell/B cell imbalance and so be useful in the therapeutic treatment of certain autoimmune diseases in which damaging antibodies are present, for example systemic lupus erythematosus and rheumatoid arthritis.

DETAILED DESCRIPTION OF THE INVENTION

The invention is directed to novel compounds having the general formula:

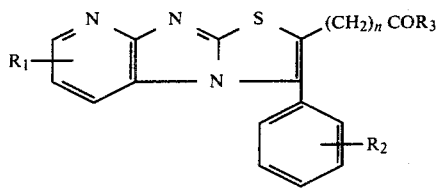

wherein $R_1$ is hydrogen, lower alkyl of 1-4 carbon atoms, $CF_3$, $NO_2$ or halo;

$R_2$ is hydrogen, lower alkyl of 1-4 carbon atoms, lower alkoxy of 1-4 carbon atoms, hydroxy, $CF_3$, halo, cycloalkyl of 5-7 carbon atoms or phenyl;

$R_3$ is lower alkoxy of 1-4 carbon atoms, hydroxy or amino; and n is 1-3.

The term halo is meant to encompass fluoro, chloro, bromo and iodo.

The compounds of the invention can be prepared according to the following reaction sequence:

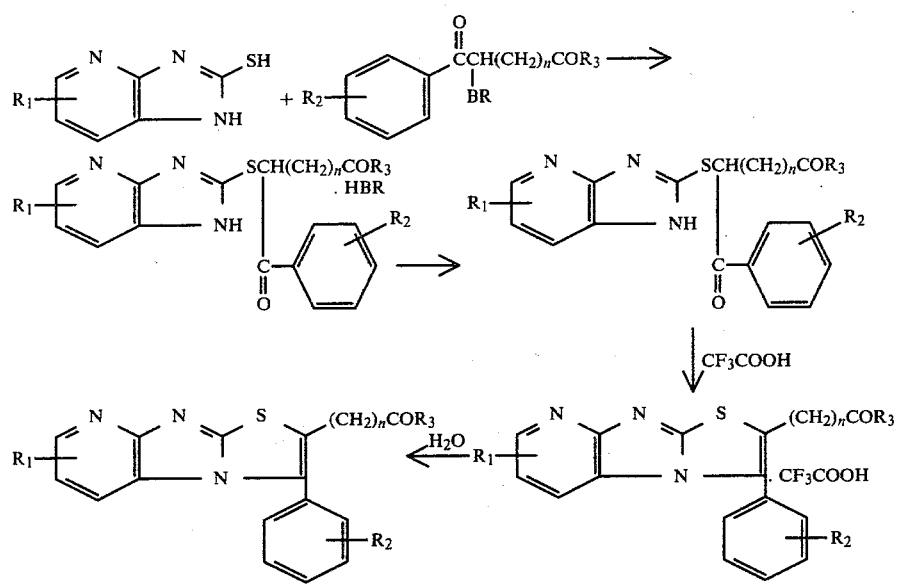

The reaction of the substituted 2-mercapto imidazo[4,5-b]pyridine with the appropriately substituted alkanoic acid or derivative thereof is carried out in an organic solvent and acetic acid. The ring closure of the thiazolo ring is carried out in the presence of a condensing agent, such as trifluoroacetic acid.

The starting substituted 2-mercapto imidazo[4,5-b]pyridine can be prepared by reacting an appropriately substituted 2,3-diaminopyridine with carbon disulfide under alkaline conditions according to the following sequence:

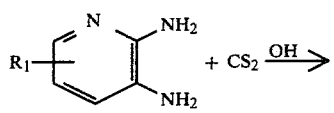

All other starting reactants are commercially available, or can be prepared according to conventional chemical procedures.

The compounds of the invention are active immunomodulators, having a stimulatory effect on the immune response. The compounds have therapeutic application in a variety of situations in which immunomodulation is indicated. Thus, the compounds are useful in the treatment of diseases involving chronic infections, in the treatment of autoimmune diseases, such as systemic lupus erythematosus and some diseases in which a condition of immune deficiency exists, such as Hodgkins disease. Further, the compounds of the invention are also of use in the treatment of conditions such as rheumatoid arthritis.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects.

The following examples show the preparation and pharmacological testing of compounds embraced by the invention.

EXAMPLE 1

2-Mercaptoimidazo[4,5-b]pyridine

To 25.25 g (0.23 m) of 2,3-diaminopyridine in water is added an aqueous solution of 31.9 g (0.57 m) KOH, followed by 35 g (0.46 m) carbon disulfide. The mixture is heated to reflux for 5 hours, after which the hot mixture is filtered and the filtrate cooled. The cold solution is acidified with acetic acid and the solid is collected, washed with water and air-dried. The crude material is recrystallized in ethanol (3500 ml) with carbon. The recrystallized material weighs 19 g (55% yield).

EXAMPLE 2

3-(Imidazo[4,5-b]pyridine-2-ylthio)-3-(4-chlorobenzoyl)propionic acid 15.1 g (0.10 m) of 2-mercaptoimidazo[4,5-b]pyridine, prepared according to Example 1, and 3-bromo-3-(4-chlorobenzoyl) propionic acid are dissolved in 1000 ml of acetone and 10 ml acetic acid. The solution is heated and concentrated to a smaller volume (about 300 ml), and some insoluble material (2-mercaptoimidazo[4,5-b]pyridine hydrobromide) is filtered off. The filtrate is concentrated to dryness and the residual solid is triturated with 500 ml acetonitrile and 150 ml acetone. A total of 30.8 g of material is obtained (77% yield), including the material recovered from the acetonitrole/acetone solutions.

30 g of the 3-(imidazo[4,5-b]pyridine-2-ylthio)-3-(4-chlorobenzoyl)propionic acid hydrobromide obtained above are dissolved in a dilute $NaHCO_3$ solution (25 g $NaHCO_3$ in 800 ml water), and the solution is filtered and the filtrate acidified with acetic acid. The solid is collected, washed well with water and air dried, yielding 20 g of material. The solid is recrystallized from hot acetonitrile. The title compound decomposes at about 140° C.

Analysis for: $C_{16}H_{12}ClN_3O_3S$: Calculated: C, 53.11; H, 3.34; N, 11.61; Cl, 9.80; S, 8.86. Found: C, 52.81; H, 3.30; N, 11.50; Cl, 9.57; S, 8.50.

EXAMPLE 3

3-(4-chlorophenyl)thiazolo[3',2':1,2]imidazo[4,5-b]pyridine-2-acetic acid 17 g (0.047 m) of 3-(imidazo[4,5-b]pyridine-2-ylthio)-3-(4-chlorobenzoyl)propionic acid, prepared according to Example 2, is dissolved in 200 ml trifluoroacetic acid, and the solution is heated to gentle reflux overnight. The solution is cooled and filtered, the solvent is removed in vacuo and the residual solid triturated with ether and the solid collected. The resulting trifluoroacetate is disproportionated in hot acetonitrile to give 9.3 g of title compound, m.p. 250°–252° C.

Analysis for: $C_{16}H_{10}ClN_3O_2S \cdot \frac{1}{2}H_2O$: Calculated: C, 54.47; H, 3.14; N, 11.91; Cl, 10.05; S, 9.09. Found: C, 54.67; H, 3.12; N, 12.08; Cl, 9.87; S, 9.39.

EXAMPLE 4

The activity of the compounds is determined according to the following procedure:

T lymphocytes are isolated from spleens of 3 month old male CBA/J mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% $CO_2$, for 45 minutes. The nonadherant T lymphocytes are then eluted from the column, counted, and adjusted to $20 \times 10^6$ cells/ml. 50 $\mu$l. of cells are cultured (37° C., 95% air, 5% $CO_2$) with a suboptimal concentration of Concanavalin A plus compound, for 48 hours before addition of 0.5 $\mu$Ci. of 3H-thymidine for the last 16 hours of culture. The total volume of the culture system is 200 $\mu$l. The cells are then harvested on a multiple automatic sample harvester (Mash II), the glass fiber filter disks placed in 10 ml. of xylene base scintillation fluid, and counted for 1 minute in a liquid scintillation counter. Results are reported as CPM±SE. Comparisons are made between counts obtained with control cultures and cultures containing compound and a determination made as to whether the compounds are active at the dosage tested.

The results are summarized below:

| Compound | Concentration ($\mu$g/culture) | 3H-Thymidine Uptake CPM + S.E. | p |
|---|---|---|---|
| Concanavalin A | 0.025 | 3,838 ± 331 | — |
| Concanavalin A + 3-(4-chlorophenyl)thiazolo[3 2:1,2]imidazo[4,5-b] | 0.05 | 11,585 ± 378 | <0.05 |
| | 0.10 | 8,055 ± 1172 | <0.05 |

| Compound | Concentration (μg/culture) | 3H-Thymidine Uptake CPM ± S.E. | p |
|---|---|---|---|
| -continued | | | |
| pyridine-2-acetic acid | 1.0 | 6,563 ± 767 | N.S. |

The results show that at low dosage levels the compound tested significantly increases lymphocyte proliferation of T cells stimulated by the mitogen, Concanavalin A, evidencing a strong stimulator activity.

What is claimed is:

1. A compound of the formula:

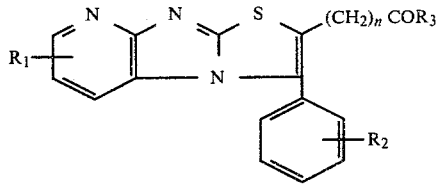

wherein
$R_1$ is hydrogen, lower alkyl of 1-4 carbon atoms, $CF_3$, $NO_2$ or halo;
$R_2$ is hydrogen, lower alkyl of 1-4 carbon atoms, lower alkoxy of 1-4 carbon atoms, hydroxy, $CF_3$, halo, cyclalkyl of 5-7 carbon atoms or phenyl;
$R_3$ is lower alkoxy of 1-4 carbon atoms, hydroxy or amino; and
n is 1-3.

2. The compound of claim 1, which is 3-(4-chlorophenyl)thiazolo[3'2':1,2]imidazo[4,5-b]pyridine-2-acetic acid.

* * * * *